United States Patent [19]
Morizumi

[11] Patent Number: 6,149,582
[45] Date of Patent: Nov. 21, 2000

[54] FRONT END STRUCTURE OF STEREOSCOPIC ENDOSCOPE

[75] Inventor: Masaaki Morizumi, Omiya, Japan

[73] Assignee: Fuji Photo Optical Co., Ltd., Saitama, Japan

[21] Appl. No.: 09/317,895

[22] Filed: May 25, 1999

[30] Foreign Application Priority Data

May 29, 1998 [JP] Japan .................................. 10-166097
Jun. 4, 1998 [JP] Japan .................................. 10-172289

[51] Int. Cl.[7] .............................. A61B 1/06; H04N 13/02
[52] U.S. Cl. ......................... 600/166; 600/111; 600/176; 348/47; 348/75; 359/827
[58] Field of Search ..................................... 600/109, 111, 600/112, 166, 176, 177, 920; 348/45, 46, 47, 48, 49, 75; 359/462, 827, 377, 376, 725

[56] References Cited

U.S. PATENT DOCUMENTS 5,702,350 12/1997 Vry et al. ................................. 600/166
5,989,185 11/1999 Miyazaki ................................. 600/166

FOREIGN PATENT DOCUMENTS 11056757 3/1999 Japan .

*Primary Examiner*—Jon Henry
*Attorney, Agent, or Firm*—Snider & Associates; Ronald R. Snider

[57] ABSTRACT

A front end structure of a stereoscopic endoscope comprises a lens barrel main body 3 having a pair of lens barrel portions 31R, 31L for holding and accommodating a pair of objective optical systems 32R, 32L so as to make them project toward an object, respectively; and a front end part main body 2 formed with a pair of holes 21R, 21L for receiving the respective lens barrel portions 31R, 31L, while the image-side end portion of the front end part main body 2 is formed like a cylinder surrounding the lens barrel main body 3. The left and right side portions 41R, 41L of the outer peripheral surface of the lens barrel main body 3 are inscribed in the cylindrical portion 26 of the front end part main body 2, so that the lens barrel main body 3 and the front end part main body 2 slidably mate with each other. As a consequence, the front end part main body 2 and the lens barrel main body 3 can be assembled to each other while in a state positioned with respect to each other with a high accuracy. One of the holes 21L and its corresponding lens barrel portion 31L may mate with each other with a play, whereby a greater tolerance in dimensions can be obtained in the making of the front end part main body 2 and lens barrel main body 3.

5 Claims, 4 Drawing Sheets

FRONT END STRUCTURE OF STEREOSCOPIC ENDOSCOPE

RELATED APPLICATIONS

This application claims the priorities of Japanese Patent Application No. 10-166097 filed on May 29, 1998 and Japanese Patent Application No. 10-172289 filed on Jun. 4, 1998, which are incorporated herein by reference.

BACKGROUND OF THE INVENTION

1. Field of the Invention

The present invention relates to a stereoscopic endoscope by which a part to be inspected such as the inside of a body cavity is stereoscopically observed by means of a pair of objective optical systems disposed at the front end of its inserting portion; and, more specifically, to a structure of the front end part of the inserting portion thereof.

2. Description of the Prior Art

Recently, surgical techniques in which endoscopes are used for observing parts to be inspected within body cavities and performing operations on diseased parts within the body cavities have been prevailing. For making diagnoses more accurately and alleviating the suffering of patients, the endoscopes have been technically improved. In particular, for performing a diagnosis more accurately within a body cavity, it is useful to obtain depth information within the body cavity. Stereoscopic endoscopes have been known to respond to such a demand.

It is important for a stereoscopic endoscope to easily combine its right and left images together and obtain an image which can readily yield a three-dimensional feel. For this purpose, while a pair of objective optical systems corresponding to the right and left eyes are assembled in the endoscope with their optical axes being parallel to each other or forming an angle of convergence therebetween, a high accuracy is required for the alignment of the objective optical systems for both eyes and other components in both cases.

However, highly accurate positioning of each optical system is hard to attain and is likely to yield numerous errors in assembly and adjustment. Also, it is problematic in that its working process becomes complicated.

For reducing such errors and simplifying the working process, it is desirable that its assembling step be configured as a unit. In the case of the front end part of the stereoscopic endoscope, its working process will be simplified if a lens barrel main body holding and accommodating the objective optical systems and a front end part main body attached to the object side thereof can be manufactured separately and assembled together easily.

SUMMARY OF THE INVENTION

In view of such circumstances, it is an object of the present invention to provide a front end structure of a stereoscopic endoscope which is hard to generate error in assembly and adjustment, while being easy to assemble and able to simplify the working process.

The present invention provides a front end structure of a stereoscopic endoscope in which a pair of objective optical systems are disposed at a front end of an inserting portion, the front end structure comprising:

a pair of lens barrel portions for holding and accommodating the pair of objective optical systems, respectively;

a lens barrel main body for supporting the pair of lens barrel portions such that the lens barrel portions project toward an object; and a front end part main body formed with a pair of insertion holes adapted to receive the pair of lens barrel portions, respectively;

wherein an image-side end portion of the front end part main body is formed like a cylinder surrounding the lens barrel main body; and wherein the lens barrel main body is formed so as to slidably mate with the front end part main body.

Here, "slidably mate" refers to a state where the front end part main body mates with the lens barrel main body so as not to shift in the diametric direction. It is not always necessary for them to mate with each other so as to come into contact with each other throughout the periphery.

Preferably, the inner peripheral surface of the front end part main body is formed with a rotation preventing protrusion for preventing the lens barrel main body from rotating with respect to the front end part main body.

Also, the present invention provides a front end structure of a stereoscopic endoscope comprising:

a lens barrel main body having a pair of projected lens barrel portions, disposed at a front end of an elongated inserting portion, for holding and accommodating a pair of objective optical systems, respectively; and a front end part main body having a pair of holes for receiving the respective lens barrel portions in a state assembled to the lens barrel main body;

wherein only one of the pair of lens barrel portions and one of the holes corresponding thereto closely mate with each other in a spigot/socket connection.

Here, "spigot/socket connection" refers to a connecting state of two members where a protrusion of one member is inserted into a depression of the other member like a spigot and a socket.

In this structure, an image-side end portion of the front end part main body may be formed like a cylinder surrounding the lens barrel main body; and the lens barrel main body may be formed so as to slidably mate with the front end part main body.

Here, the inner peripheral surface of the front end part main body is preferably formed with a rotation preventing protrusion for preventing the lens barrel main body from rotating with respect to the front end part main body.

DESCRIPTION OF THE PREFERRED EMBODIMENTS

In the following, embodiments of the present invention will be explained with reference to the accompanying drawings.

The front end structure of the stereoscopic endoscope in accordance with these embodiments is employed in a so-called electronic endoscope apparatus in which a front end part of the inserting portion of the endoscope has a solid-state imaging device (CCD).

Namely, in this electronic endoscope apparatus, a luminous flux carrying subject information incident on an objective optical system from the front end side of the elongated inserting portion adapted to be inserted into a body cavity or the like is focused onto a CCD, the video signal data captured by the CCD is transmitted to a control unit connected to an operating section and is subjected to signal processing in the control unit, and then the subject image is displayed on a monitor.

On the monitor, right- and left-eye images having a parallax with respect to each other are displayed alternately. By viewing these color images through a pair of shutter glasses, a viewer can see the subject image three-dimensionally. The inserting portion is provided with an illumination light transmitting means for supplying illumination light from a light source apparatus, and an illumination optical system for emitting thus transmitted light through an illumination window so as to illuminate the subject.

Figure 1:
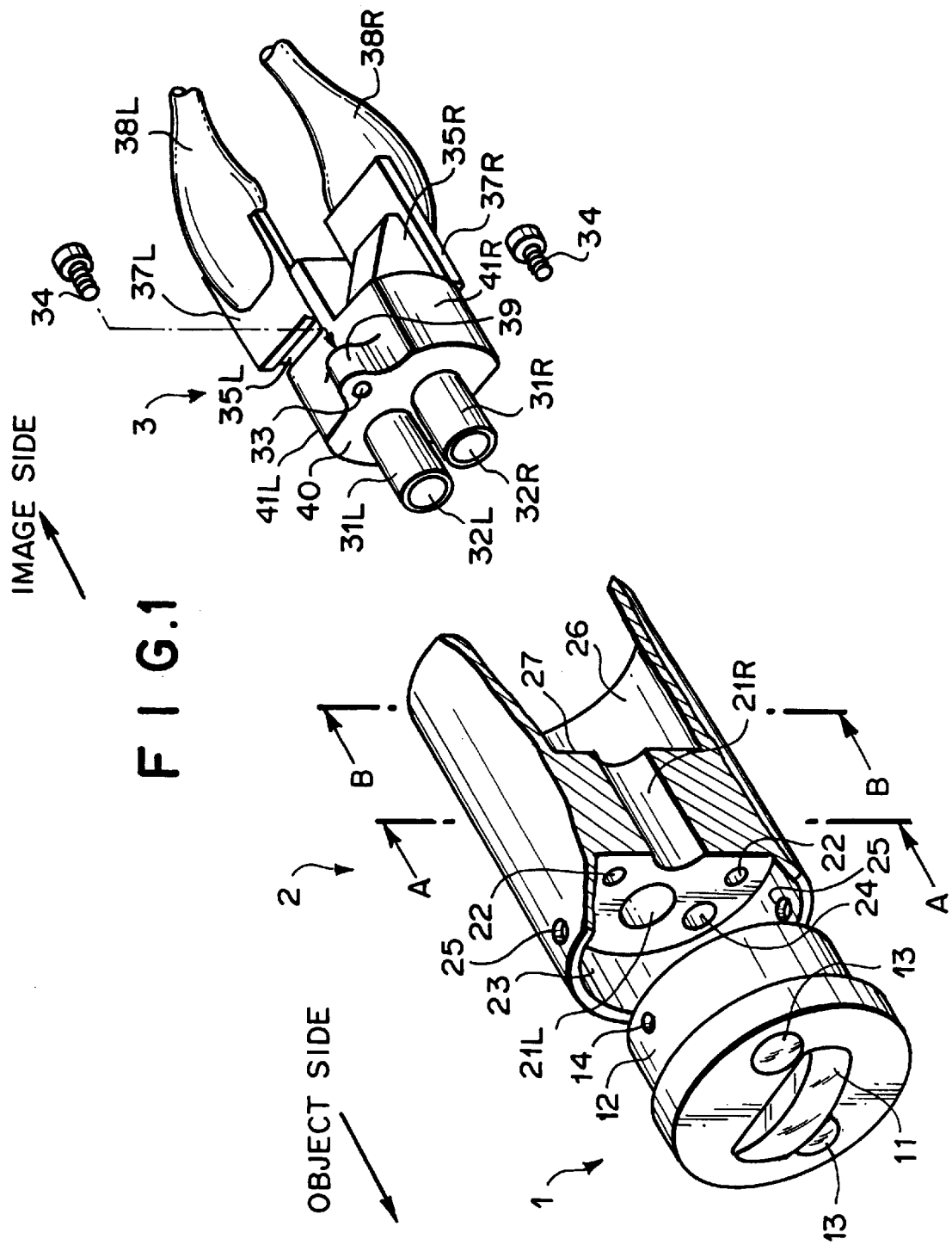
FIG. 1 is a perspective view showing the front end structure of the stereoscopic endoscope in accordance with an embodiment of the present invention.

FIG. 1 is a view showing the front end structure of the stereoscopic endoscope in accordance with an embodiment of the present invention.

The front end portion of this stereoscopic endoscope comprises, successively from the object side, a front end part 1, a front end part main body 2, and a lens barrel main body 3.

The front end part 1 is used as being assembled to the object side of the front end part main body 2. It comprises a front end lens 11, and illumination windows 13 located on both sides thereof.

A protrusion 12 of the front end part 1 and a depression 23 of the front end part main body 2 mate with each other in a spigot/socket connection. At the positions where tapped holes 14 and 25 formed at two locations each of the front end part 1 and the front end part main body 2 on the upper and lower sides meet, the tapped holes 14, 25 are engaged with not-illustrated screws, whereby the front end part 1 and the front end part main body 2 are secured to each other.

The front end part main body 2 comprises a pair of lens barrel part insertion holes 21R, 21L formed parallel to each other; holes 24 for the illumination light transmitting means; and tapped holes 22 for securing the lens barrel main body 3 assembled to the image side of the front end part main body 2. The image-side end portion of the front end part main body 2 is formed with a cylindrical portion 26 extending toward the image side.

The lens barrel main body 3 comprises two tapped holes 33 formed in upper and lower flanges 39, respectively, for securing the front end part main body 2; a pair of lens barrel portions 31R, 31L, formed so as to project from a front wall face 40 of the lens barrel main body 3 including the front faces of the flanges 39 toward the front end part main body 2, for holding and accommodating a pair of objective optical systems 32R, 32L, respectively; a pair of circuit boards 37R, 37L mounting a pair of CCDs 36R, 36L (see FIG. 3), respectively; and a pair of rectangular prisms 35R, 35L for deflecting luminous fluxes from the objective optical systems 32R, 32L so as to make them incident on the CCDs 36R, 36L, respectively. The incident luminous fluxes carrying subject information from the object side are focused onto the imaging surfaces of the CCDs 36R, 36L, subjected to photoelectric conversion, and then transmitted as image data to a not-illustrated control unit by way of a pair of cables 38R, 38L drawn from the circuit boards 37R, 37L, respectively.

Figure 2:
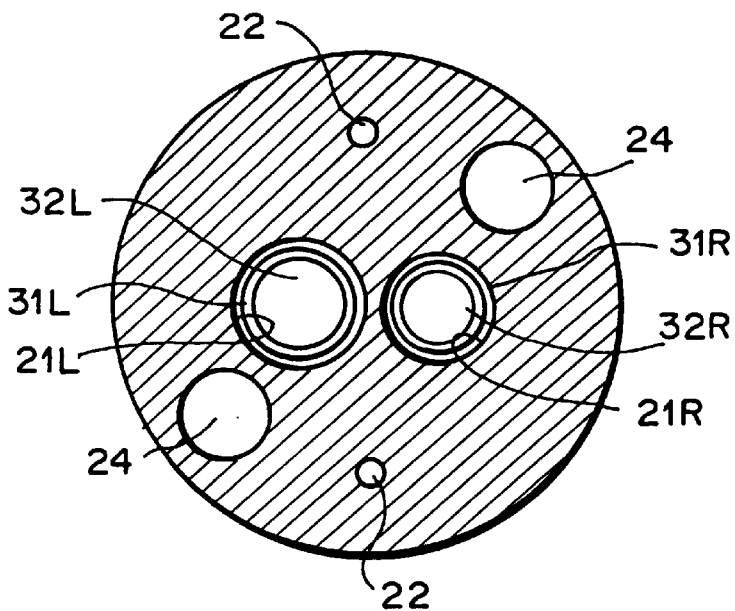
FIG. 2 is a sectional view taken along the line A—A of FIG. 1.

FIG. 2 shows a sectional view taken along the line A—A of FIG. 1. The front end part main body 2 and the lens barrel main body 3 are assembled to each other such that the lens barrel part insertion holes 21R, 21L are combined with their corresponding lens barrel portions 31R, 31L, each with a play. After being thus assembled to each other in a predetermined state, the front end part main body 2 and the lens barrel main body 3 are secured to each other as the tapped holes 33 of the flanges 39 formed at the upper and lower locations and the tapped holes 22 formed in the front end part main body 2 are engaged with fastening screws 34. Thus, the lens barrel main body 3 is inserted into the front end part main body 2 such that the front wall face 40 of the former and the bottom wall face 27 of the cylindrical portion 26 of the latter abut to each other, and they are screwed and secured to each other. Such securing enhances the screwing strength of the fastening screws 34, so that their holding states become favorable, and the axial positioning becomes easier, while dislocation is hard to occur.

Figure 4:
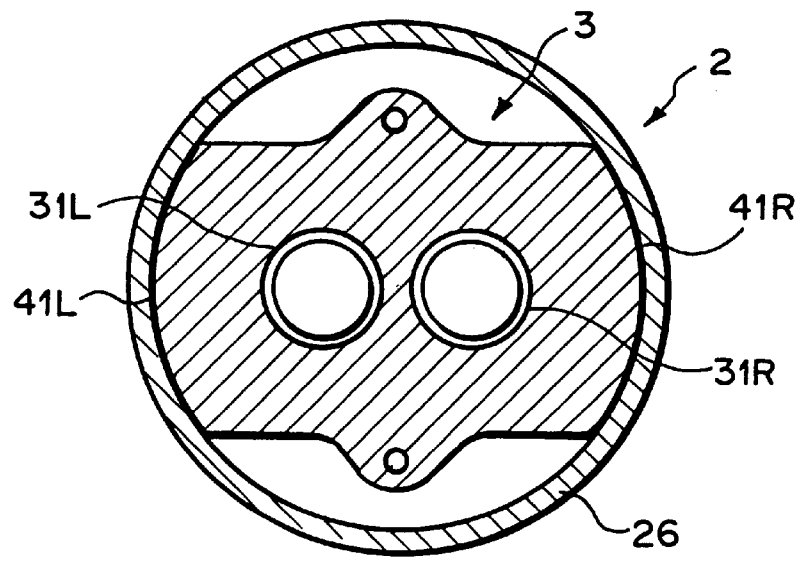
FIG. 4 is a sectional view taken along the line B—B of FIG. 1.

FIG. 4 shows a sectional view taken along the line B—B of FIG. 1. In the outer peripheral surface of the lens barrel main body 3, its right and left side portions 41R, 41L are formed as a part of a cylindrical surface having an outside diameter substantially the same as the inside diameter of the cylindrical portion 26 of the front end part main body 2, whereby the lens barrel main body 3 is allowed to slidably mate with the front end part main body 2. The axial length of the cylindrical portion 26 is set longer than the lens barrel portion 31R, 31L.

In the following, the configuration of optical system in accordance with this embodiment will be explained.

Figure 3:
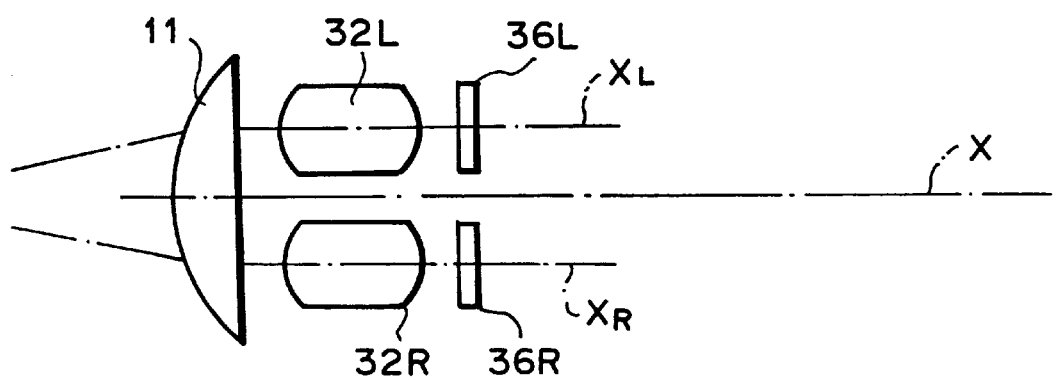
FIG. 3 is a conceptual view of an optical system in the embodiment shown in FIG. 1.

In the optical system used in the front end structure of the stereoscopic endoscope in accordance with this embodiment, the respective optical axes of the pair of objective optical systems 32R, 32L are parallel to each other as shown in FIG. 3.

In general, when images for right and left eyes obtained by a pair of objective optical systems form an angle therebetween approximating the angle of convergence upon viewing by both eyes of a viewer, their three-dimensional feel becomes favorable, and the viewer feels less fatigue. However, if a configuration in which the optical axes of the objective optical systems have an angle of convergence with respect to each other is employed for the sake of easiness in viewing, the working process will be complicated, and errors upon assembly and adjustment will increase.

Therefore, it is desirable to construct, as in this embodiment, for example, an optical system in which the front end lens 11 is disposed on the object side of the objective optical systems 32R, 32L such that an angle of convergence can be obtained for right and left eyes while the respective optical axes of the objective optical systems 32R, 32L are parallel to each other. Here, the front end lens 11 is a lens having a focal length corresponding to the distance to the subject, and a positive refracting power; whereas the objective optical systems 32R, 32L are combined to each other so as to form an image at infinity. When the optical axes are disposed parallel to each other, the assembling step can easily be configured as a unit, errors in assembly and adjustment can be reduced, and the cost can be cut down.

Figure 7:
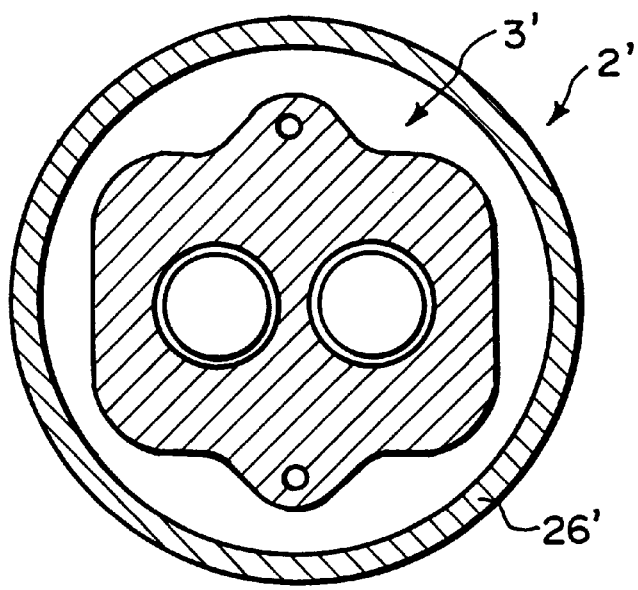
FIG. 7 is a sectional view showing a conventional example.

In the case of the front end structure of the stereoscopic endoscope in which the front end lens 11 is disposed, the front end part 1 and the front end part main body 2 mate with each other in a spigot/socket connection, whereas the front end part main body 2 and the lens barrel main body 3 slidably mate with each other. Consequently, as compared with a conventional front end structure shown in FIG. 7 (in which a lens barrel main body 3' is simply accommodated within a cylindrical portion 26' of a front end part main body 2'), assembling can be carried out in a state where a high accuracy and numerical control are attained in the optical-axis alignment of the front end lens 11, the objective optical systems 32R, 32L, and the CCDs 36R, 36L, or the like.

Also, since the axial length of the cylindrical portion 26 is set longer than the lens barrel portion 31R, 31L of the lens barrel main body 3, the front end part main body 2 can perform a guiding function when the lens barrel portions 31R, 31L are inserted into their corresponding lens barrel insertion holes 21R, 21L as the front end part main body 2 and the lens barrel main body 3 slidably mate with each other.

Though the front end part 1 of this embodiment is provided with the illumination windows 13 separately from the front end lens 11, the form of the front end lens 11 may be changed as required without providing the illumination windows 13, such that the illumination light passes through a peripheral portion of the front end lens 11.

The front end part 1 and the front end part main body 2 may be integrated with each other. Also, the tapped holes 22 may not be through holes.

Figure 5:
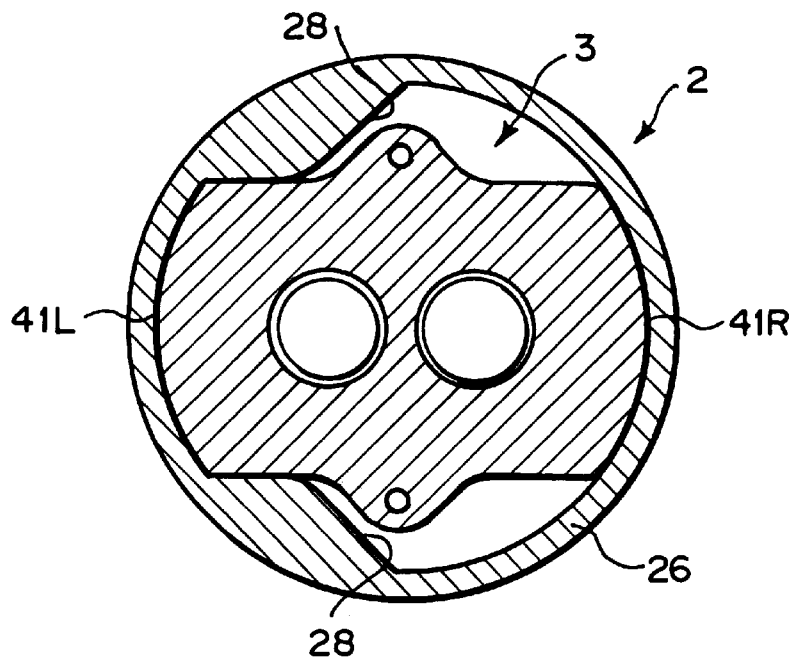
FIG. 5 is a sectional view showing a modified example of the embodiment shown in FIG. 1.

FIG. 5 is a schematic view showing a modified example of this embodiment.

In this modified example, a pair of rotation preventing protrusions 28 are formed on the upper and lower sides of the left-side outer peripheral surface portion 41L of the lens barrel main body 3 in the inner peripheral surface of the cylindrical portion 26 of the front end part main body 2. The pair of rotation preventing protrusions 28 hold the left-side outer peripheral portion 41L from upper and lower sides thereof, thereby preventing the lens barrel main body 3 from rotating with respect to the front end part main body 2.

Figure 6:
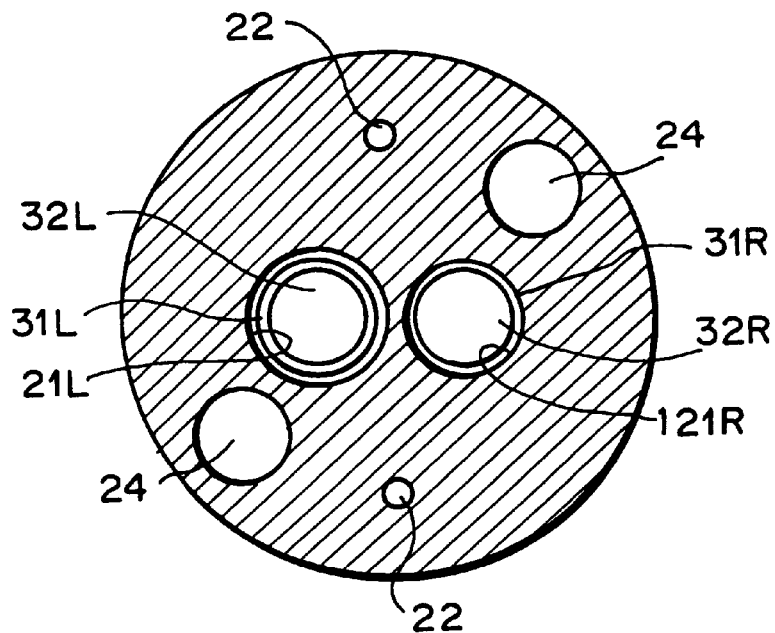
FIG. 6 is a sectional view taken along the line A—A of FIG. 1, showing an embodiment different from that shown in FIG. 2.

FIG. 6 is a sectional view taken along the line A—A of FIG. 1, showing another embodiment of the present invention. When assembling the front end part main body 2 and the lens barrel main body 3 to each other, only one of the combination of a lens barrel accommodating portion 121R and its corresponding lens barrel portion 31R and the combination of a lens barrel accommodating portion 21L and its corresponding lens barrel portion 31L may closely mate with each other in a spigol/socket connection, whereas the other is set to a mating state with a play, as with this embodiment. In this embodiment, the lens barrel accommodating portion 121R and the lens barrel portion 31R closely mate with each other in a spigot/socket connection. They constitute a basic mating portion which acts as a basis at the time of assembling. The other lens barrel accommodating portion 21L and the lens barrel portion 31L are assembled together with a play therebetween. After being thus positioned and assembled together in a predetermined state, the front end part main body 2 and the lens barrel main body 3 are secured to each other as both of the tapped holes 33 in the flanges 39 formed at the upper and lower locations and the tapped holes 22 formed in the front end part main body 2 are engaged with the fastening screws 34.

When the lens barrel accommodating portion 121R and the lens barrel portion 31R closely mate with each other in a spigot/socket connection, then the front part main body 2 and the lens barrel main body 3 are connected to each other without dislocating from each other in the axial and rotational directions. If both right and left lens barrel accommodating portions 121R, 21L are to be closely mated with their corresponding lens barrel portions 31R, 31L in a spigot/socket connection, then a very high accuracy in alignment will be necessary, whereby assembling will become more difficult. Thus, when the members in one of the combinations closely mate with each other in a spigot/socket connection, whereas a space is left to form a play in the other combination, a greater tolerance in dimensions can be attained in the making of the front end part main body 2 and lens barrel main body 3, whereby their manufacture and assembly become easier. Also, as the members in one of the combinations closely mate with each other in a spigot/socket connection, their holding strength enhances, whereby the stress applied to the fastening screws 34 can be lowered.

As explained in the foregoing, the front end structure of the stereoscopic endoscope in accordance with the present invention comprises a pair of lens barrel portions for holding and accommodating a pair of objective optical systems, respectively; a lens barrel main body for supporting the pair of lens barrel portions such that the lens barrel portions project toward an object; and a front end part main body formed with a pair of insertion holes adapted to receive the pair of lens barrel portions, respectively; while an image-side end portion of the front end part main body is formed like a cylinder surrounding the lens barrel main body; and the lens barrel main body is formed so as to slidably mate with the front end part main body. Therefore the front end part main body and the lens barrel main body can be assembled to each other in a state positioned to each other with a high accuracy. As a consequence, the front end part of the inserting portion of the endoscope can become hard to generate errors in assembly or adjustment while being easy to assemble and able to simplify the working process.

Here, when the inner peripheral surface of the front end part main body is formed with a rotation preventing protrusion, so as to prevent the lens barrel main body from rotating with respect to the front end part main body, the front end part main body and the lens barrel main body can be assembled to each other more easily.

Further, the front end structure of the stereoscopic endoscope in accordance with the present invention may be configured such that one of the pair of lens barrel portions and its corresponding lens barrel accommodating portion in a pair of lens barrel accommodating portions closely mate with each other in a spigot/socket connection, while the other lens barrel portion and lens barrel accommodating portion mate with each other with a play. This configuration can also yield a front end structure of the endoscope which is hard to generate errors in assembly or adjustment while being easy to assemble and able to simplify the working process.

What is claimed is:

1. A front end structure of a stereoscopic endoscope in which a pair of objective optical systems are disposed at a front end of an inserting portion, said front end structure comprising:

a pair of lens barrel portions for holding and accommodating said pair of objective optical systems, respectively;

a lens barrel main body for supporting said pair of lens barrel portions such that said lens barrel portions project toward an object; and a front end part main body formed with a pair of insertion holes adapted to receive said pair of lens barrel portions, respectively;

wherein an image-side end portion of said front end part main body is formed like a cylinder surrounding said lens barrel main body; and wherein said lens barrel main body is formed so as to slidably mate with said front end part main body.

2. A front end structure of a stereoscopic endoscope according to claim 1, wherein an inner peripheral surface of said front end part main body is formed with a rotation preventing protrusion for preventing said lens barrel main body from rotating with respect to said front end part main body.

3. A front end structure of a stereoscopic endoscope comprising:

a lens barrel main body having a pair of projected lens barrel portions, disposed at a front end of an elongated inserting portion, for holding and accommodating a pair of objective optical systems, respectively; and a front end part main body having a pair of holes for receiving said respective lens barrel portions in a state assembled to said lens barrel main body;

wherein only one of said pair of lens barrel portions and one of said holes corresponding thereto closely mate with each other in a spigot/socket connection.

4. A front end structure of a stereoscopic endoscope according to claim 3, wherein an image-side end portion of said front end part main body is formed like a cylinder surrounding said lens barrel main body; and wherein said lens barrel main body is formed so as to slidably mate with said front end part main body.

5. A front end structure of a stereoscopic endoscope according to claim 4, wherein an inner peripheral surface of said front end part main body is formed with a rotation preventing protrusion for preventing said lens barrel main body from rotating with respect to said front end part main body.

* * * * *